US012779236B2

(12) United States Patent
Wong et al.

(10) Patent No.: US 12,779,236 B2
(45) Date of Patent: Nov. 3, 2026

(54) SYSTEM FOR TREATING UNWANTED TISSUE

(71) Applicant: IKOMED TECHNOLOGIES INC., Vancouver (CA)

(72) Inventors: Kar-Pan Wong, Vancouver (CA); Eran Elizur, Vancouver (CA); Evan Goodacre, Vancouver (CA); Susanna Kim Wolff, Vancouver (CA); Daniel Gelbart, Vancouver (CA)

(73) Assignee: IKOMED TECHNOLOGIES INC., Vancouver (CA)

( * ) Notice: Subject to any disclaimer, the term of this patent is extended or adjusted under 35 U.S.C. 154(b) by 818 days.

(21) Appl. No.: 17/994,275

(22) Filed: Nov. 25, 2022

(65) Prior Publication Data

US 2023/0158319 A1 May 25, 2023

Related U.S. Application Data

(63) Continuation of application No. PCT/CA2021/050721, filed on May 27, 2021.

(Continued)

(51) Int. Cl.
*A61N 1/40* (2006.01)
*A61B 5/055* (2006.01)
*A61N 1/08* (2006.01)

(52) U.S. Cl.
CPC .............. *A61N 1/403* (2013.01); *A61B 5/055* (2013.01); *A61N 1/086* (2017.08)

(58) Field of Classification Search
CPC .... A61N 1/403; A61N 1/086; A61N 1/36031; A61B 2018/00541; A61B 5/053;

(Continued)

(56) References Cited

U.S. PATENT DOCUMENTS 2,249,935 A 7/1941 Birtcher
2,276,996 A 3/1942 Milinowski (Continued)

FOREIGN PATENT DOCUMENTS

CN 1477985 2/2004
CN 103025262 A 4/2013

(Continued)

OTHER PUBLICATIONS

JP-2005296584-A (translated) (Year: 2005).*

(Continued)

*Primary Examiner* — Joseph A Stoklosa
*Assistant Examiner* — Ashleigh Lauren Kern
(74) *Attorney, Agent, or Firm* — Todd A. Rattray; Oyen Wiggs Green & Mutala LLP

(57) ABSTRACT

The present technology may be applied to selectively heat one or more diseased areas in the lung while limiting heating to the healthy area and surrounding tissue. This heating provides a therapeutic effect. The selective heating of diseased tissues may be achieved by exposing the lung to an electromagnetic field to cause dielectric or eddy current heating. The present technology is particularly useful for treating emphysema as the diseased areas in emphysema patients have reduced blood flow. The diseased areas will heat up rapidly while the healthy tissue will be cooled by blood flow. This is particularly effective for treating emphysema because of the low mass of the lungs and the high blood flow. In one described embodiment the frequency of the electromagnetic radiation is selected to satisfy certain resonance conditions of the apparatus. In another described embodiment the electromagnetic radiation is applied with a coil whose geometric parameters are chosen so as to produce an electric field maximum in the area to be heated. In another described embodiment the electromagnetic radiation is (Continued)

applied with a pair of electromagnetic energy signal applicators which are positioned around the torso of the patient, one positioned cranially from the treated area and the other positioned caudally from the treated area, and which are shaped to wrap or partially wrap around the circumference of the torso.

28 Claims, 4 Drawing Sheets

Related U.S. Application Data

(60) Provisional application No. 63/030,879, filed on May 27, 2020.

(58) Field of Classification Search
CPC ... A61B 5/0803; A61B 5/4836; A61B 8/5223; A61B 5/055; A61B 5/6848; A61B 5/6852; A61B 2018/00642; A61B 2018/00791; A61B 5/01; A61B 8/00; A61B 18/04; A61B 2018/00017; A61B 2018/00029; A61B 2018/00577; A61B 2018/00702
See application file for complete search history.

(56) References Cited

U.S. PATENT DOCUMENTS

| | | | | |
|---|---|---|---|---|
| 2,549,399 | A | | 4/1951 | Tawney |
| 3,638,657 | A | | 2/1972 | Mettler |
| 3,747,013 | A | | 7/1973 | Mettler |
| 3,800,802 | A | | 4/1974 | Berry et al. |
| 3,927,557 | A | | 12/1975 | Viertl |
| 4,269,199 | A | | 5/1981 | Armitage |
| 4,298,009 | A | | 11/1981 | Mezrich et al. |
| 4,305,115 | A | | 12/1981 | Armitage |
| 4,527,550 | A | * | 7/1985 | Ruggera ................ A61N 1/403 219/674 |
| 4,632,127 | A | | 12/1986 | Sterzer |
| 4,685,462 | A | * | 8/1987 | Olsen ....................... A61N 2/00 607/98 |
| 4,798,215 | A | | 1/1989 | Turner |
| 5,010,897 | A | | 4/1991 | Leveen |
| 5,117,829 | A | | 6/1992 | Miller et al. |
| 5,364,392 | A | | 11/1994 | Warner et al. |
| 5,451,221 | A | | 9/1995 | Cho et al. |
| 5,503,150 | A | | 4/1996 | Evans |
| 5,571,154 | A | | 11/1996 | Ren |
| 6,181,970 | B1 | | 1/2001 | Kasevich |
| 6,312,426 | B1 | | 11/2001 | Goldberg et al. |
| 6,328,689 | B1 | | 12/2001 | Gonzalez et al. |
| 6,330,479 | B1 | | 12/2001 | Stauffer |
| 6,428,532 | B1 | | 8/2002 | Doukas et al. |
| 6,610,043 | B1 | | 8/2003 | Ingenito |
| 6,613,005 | B1 | | 9/2003 | Friedman et al. |
| 6,692,494 | B1 | | 2/2004 | Cooper et al. |
| 6,709,401 | B2 | | 3/2004 | Perkins et al. |
| 6,712,816 | B2 | | 3/2004 | Hung et al. |
| 6,853,865 | B2 | | 2/2005 | Beens et al. |
| 6,997,918 | B2 | | 2/2006 | Soltesz et al. |
| 7,004,940 | B2 | | 2/2006 | Ryan et al. |
| 7,300,428 | B2 | | 11/2007 | Ingenito |
| 7,412,977 | B2 | | 8/2008 | Fields et al. |
| 7,587,230 | B2 | | 9/2009 | Litovitz |
| 7,770,584 | B2 | | 8/2010 | Danek et al. |
| 7,953,500 | B2 | | 5/2011 | Bingham et al. |
| 7,979,139 | B2 | | 7/2011 | Beens et al. |
| 8,444,635 | B2 | | 5/2013 | Lichtenstein et al. |
| 8,467,858 | B2 | | 6/2013 | Vertikov et al. |
| 8,585,645 | B2 | | 11/2013 | Bany et al. |
| 9,028,482 | B2 | | 5/2015 | Collins |
| 9,113,858 | B2 | | 8/2015 | Barry et al. |
| 9,192,422 | B2 | | 11/2015 | Collins |
| 9,962,225 | B2 | | 5/2018 | McMillan |
| 10,953,235 | B2 | | 3/2021 | Anderson et al. |
| 2003/0018327 | A1 | | 1/2003 | Truckai et al. |
| 2004/0047855 | A1 | | 3/2004 | Ingenito |
| 2005/0038339 | A1 | | 2/2005 | Chauhan et al. |
| 2005/0085801 | A1 | | 4/2005 | Cooper et al. |
| 2005/0281800 | A1 | | 12/2005 | Gong et al. |
| 2006/0047291 | A1 | | 3/2006 | Barry |
| 2006/0135947 | A1 | | 6/2006 | Soltesz et al. |
| 2006/0161233 | A1 | | 7/2006 | Barry et al. |
| 2006/0259103 | A1 | | 11/2006 | Stenzel |
| 2007/0043350 | A1 | | 2/2007 | Soltesz et al. |
| 2007/0208399 | A1 | | 9/2007 | Turner et al. |
| 2008/0033412 | A1 | | 2/2008 | Whelan et al. |
| 2008/0097139 | A1 | | 4/2008 | Clerc et al. |
| 2008/0132826 | A1 | | 6/2008 | Shadduck et al. |
| 2008/0154252 | A1 | | 6/2008 | Torchia et al. |
| 2008/0167555 | A1 | | 7/2008 | Qian et al. |
| 2008/0228137 | A1 | | 9/2008 | Aljuri et al. |
| 2008/0249503 | A1 | | 10/2008 | Fields et al. |
| 2010/0042020 | A1 | | 2/2010 | Ben-Ezra |
| 2010/0125225 | A1 | | 5/2010 | Gelbart et al. |
| 2011/0054431 | A1 | | 3/2011 | Turnquist et al. |
| 2011/0060393 | A1 | | 3/2011 | Azure et al. |
| 2011/0301450 | A1 | | 12/2011 | Hue et al. |
| 2012/0089209 | A1 | | 4/2012 | Schoenbach et al. |
| 2012/0157838 | A1 | * | 6/2012 | Adanny ................... A61B 5/01 600/438 |
| 2013/0016679 | A1 | | 1/2013 | Yu et al. |
| 2013/0261621 | A1 | | 10/2013 | Kramer et al. |
| 2015/0018817 | A1 | | 1/2015 | Willard |
| 2016/0184013 | A1 | | 6/2016 | Brannan et al. |
| 2017/0143414 | A1 | | 5/2017 | Sliwa et al. |
| 2018/0000533 | A1 | | 1/2018 | Boll et al. |
| 2018/0015294 | A1 | | 1/2018 | Anderson, Jr. et al. |
| 2019/0030356 | A1 | | 1/2019 | Schwarz |
| 2019/0090928 | A1 | * | 3/2019 | Lichtenstein ........ A61B 5/0036 |

FOREIGN PATENT DOCUMENTS

| | | | | |
|---|---|---|---|---|
| EP | 1658818 | | | 5/2006 |
| EP | 12094207 | B1 | | 9/2015 |
| JP | H07-155384 | | | 6/1995 |
| JP | 07231895 | | | 9/1995 |
| JP | 2005296584 | | | 10/2005 |
| JP | 2005296584 | A | * | 10/2005 |
| KR | 10-20110026244 | A | | 3/2011 |
| KR | 10-1080603 | B1 | | 11/2011 |
| WO | 03047603 | A2 | | 6/2003 |
| WO | 2004022160 | A1 | | 3/2004 |
| WO | 2016109437 | A1 | | 7/2016 |
| WO | 2016119033 | A2 | | 8/2016 |
| WO | 2017201625 | A1 | | 11/2017 |

OTHER PUBLICATIONS

JP-2005296584-A (translated) (Year: 2004).*

JP_2005296584_A (Year: 2005).*

P. Gebhardt, FPGA-based RF interference reduction techniques for simultaneous PET—MRI, Apr. 6, 2016, 1OP Publishing, vol. 61, pp. 3500-3526 (Year: 2016).

* cited by examiner

SYSTEM FOR TREATING UNWANTED TISSUE

CROSS-REFERENCE TO RELATED APPLICATIONS

This application is a continuation of Patent Cooperation Treaty (PCT) application No. PCT/CA2021/050721 having an international filing date of 27 May 2021 and entitled SYSTEM FOR TREATING UNWANTED TISSUE, which in turn claims priority from, and for the purposes of the United States of America claims the benefit under 35 U.S.C. § 119 of, U.S. application No. 63/030,879 filed 27 May 2020 and entitled SYSTEM FOR TREATING UNWANTED TISSUE. All of the applications referred to in this paragraph are hereby incorporated herein by reference.

FIELD

The invention relates to medical devices and methods for treating unwanted tissues. The invention has example application in treating lung diseases such as chronic obstructive pulmonary disease (COPD), one example of which is emphysema.

BACKGROUND

There are a variety of medical conditions for which treatment can include destroying or affecting a non-desired tissue. Such treatments should ideally avoid harming normal tissues adjacent to the non-desired tissue. For example, some lung conditions can benefit from treatments that involve destroying or affecting diseased lung tissue. Some of these treatments involve heating the lung tissue. Background information on lung disease can be found in medical textbooks, such as "Pulmonary Pathophysiology" by Dr. John B. West, ISBN 0-683-08934-X.

Emphysema is a disease that damages the alveoli (air sacs) in a patient's lungs.

Emphysema can cause the alveoli in the patient's lungs to rupture. This alters the distribution of air spaces in the lungs and reduces the surface area of the lungs available to take up oxygen. The lung damage caused by emphysema can trap stale air in the lungs and/or reduce the flow of fresh, oxygen-rich air into the lungs. In a patient suffering from emphysema, diseased parts of the patient's lungs are not effectively ventilated through the bronchi and trachea, thus preventing the lungs from fully deflating and inflating. Air trapped inside the lungs can prevent the diaphragm from moving up and down naturally. This condition results in difficulty breathing and an overall reduced health and life quality.

Some prior art approaches to heating diseased tissue within the lung involve inserting an ablation device through the trachea and bronchi into the diseased area (for example, see Brannan et al. US 2016/0184013). This approach has various shortcomings: only a small part of the lung is accessible, precise mapping of the diseased area is required, and the ablation device must be accurately guided to a precise location. In addition, during treatment, collateral damage is caused to tissue located along the path of the device from the point of entry to the point of treatment.

Some prior references in the general field of the invention are:

a) Lichtenstein et al., U.S. Pat. No. 8,444,635, which is hereby incorporated herein by reference, discloses a system that exposes undesired tissue to a scanning focused microwave beam.

b) Palti, U.S. Pat. No. 8,019,414 discloses combining chemotherapy treatment with low intensity, intermediate frequency alternating electric fields that are tuned to a particular type of target cell.

c) Armitage, U.S. Pat. No. 4,269,199 discloses a method for inducing local hyperthermia in treatment of a tumor by short wave diathermy. The method involves moving an induction coil over the portion of the body containing the tumor such that the axis of the coil constantly transects different portions of the tumor.

d) Turner, U.S. Pat. No. 4,798,215 discloses a combined hyperthermia treatment and non-invasive thermometry apparatus.

e) Leveen, U.S. Pat. No. 5,010,897 discloses an apparatus for the deep heating of cancers. The apparatus employs two single turn coaxial coils which rotate synchronously in planes which are parallel to each other with the central axis of each coil lying in exactly the same line which is perpendicular to the plane of the coil. The combined magnetic field of the rotating coils continuously heats a tumor.

f) Evans, U.S. Pat. No. 5,503,150 discloses an apparatus and method for noninvasively locating and heating a volume of tissue that includes the ability to detect temperature changes in the volume of tissue.

g) Kasevich, U.S. Pat. No. 6,181,970 discloses medical systems and instruments which utilize microwave energy to provide heat treatment and diagnostic imaging of tissue.

h) Barry et al., U.S. Pat. No. 8,585,645 discloses treating locations in a patient's lung using high temperature vapor delivered through the inner lumen of a catheter.

i) Turnquist et al., US2011/0054431 discloses devices and methods to non-invasively heat bodily tissues and fluid using emitted energy and non-invasively measure the resulting temperature changes in the target and surrounding fluid and tissue to detect and/or treat for various physical conditions, such as, for example, vesicoureteral reflux.

j) Lichtenstein et al. WO 2017/201625 describes methods and apparatus that can be used to heat tissues to treat emphysema with energy delivered through external electrodes or coils.

k) Vertikov et al., U.S. Pat. No. 8,467,858 describes devices and techniques for thermotherapy based on optical imaging.

l) Ruggera et al. CA1212424A describes a helical coil for diathermy apparatus driven by frequencies corresponding to integral multiples of one-half the basic wavelength, to achieve transverse uniform heating and enable shifting the heat focus volume along the coil axis from the normal centered location on the axis produced by full-wave excitation.

There is a general desire for systems that can automatically heat tissues in diseased areas. There is a general desire for systems which can heat tissues in diseased areas without having to locate the diseased areas precisely. There is a particular need for new practical methods and apparatus for heating all diseased parts of the lung without excessively heating healthy parts of the lung or surrounding healthy tissues.

SUMMARY

This invention has a number of aspects. These aspects include, without limitation:

- Apparatus useful for selectively heating tissues within a patient.
- Control systems for tissue heating apparatus;
- Methods for controlling apparatus for selectively heating tissues within a patient;
- Methods for treating a patient which include the selective heating of tissues within the patient.
- Uses of apparatus for treatment of COPD and other lung diseases.

An example and non-limiting application of methods and apparatus as described herein is treatment of diseased lung tissues, for example, lung tissues affected by emphysema or other forms of COPD. Some embodiments provide methods and/or apparatus that are particularly adapted for selectively heating lung tissues to treat COPD and/or other diseases of the lungs.

One aspect of the invention provides an apparatus for treating emphysema or COPD by selectively heating diseased lung tissue in a patient to a treatment temperature sufficient to cause a therapeutic effect in the diseased lung tissue, the apparatus comprising: at least one signal applicator comprising an electrical conductor dimensioned to extend circumferentially around or nearly around the torso of the patient; a power source connected to deliver a radiofrequency (RF) signal to the at least one applicator, the power source comprising an impedance matching network operative to match an output impedance of the power source to an input impedance of the signal applicator; a controller operatively associated with the power source and configured to control the power source to apply the RF signal to the applicator; the applicator, when energized by the RF signal, operative to couple an electromagnetic energy signal into tissues of the patient, such that the tissues of the patient are heated by the electromagnetic energy signal and the diseased tissue is selectively heated to higher temperatures than healthy tissues due to relatively lower blood circulation to the diseased tissue.

In some embodiments the power source has a maximum RF signal output power of at least 500 watts. In some embodiments the RF signal creates a localized axial electric or magnetic field within lungs of the patient. This localized field may serve as a primary source of (dielectric) heating of the tissues of the patient.

In some embodiments, the temperature monitor is operative to monitor a temperature at one or more locations within the tissue of the patient wherein the controller is connected to receive a temperature signal from the temperature monitor indicating a temperature at the one or more locations, and the controller is configured to apply feedback control to the power source to regulate the electromagnetic energy signal delivered into the patient based at least in part on the temperature signal.

In some embodiments, the temperature monitor is a non-invasive temperature monitor.

In some embodiments, the temperature monitor comprises a magnetic resonance imaging (MRI) imaging system and a processor configured to process a MRI signal provided by the MRI imaging system to determine the temperature corresponding to each of the one or more locations.

In some embodiments, the temperature monitor comprises an ultrasound imaging (US) system and a processor configured to process an ultrasound signal provided by the US imaging system to determine the temperature corresponding to each of the one or more locations.

In some embodiments, the controller is configured to control one or more parameters of the RF signal until the temperature at the location is at least equal to the treatment temperature.

In some embodiments, the controller comprises a thermal model of at least a portion of the patient, the thermal model correlating temperatures at the one or more locations to a temperature of a location of interest and the controller is configured to apply the thermal model using the temperature signal as an input and to regulate the heating energy based at least in part on an output of the thermal model.

In some embodiments, the thermal model comprises one or more of: electrical and thermal properties of different tissue types in the patient, distributions of the different tissue types in the patient, geometry of the one or more electromagnetic energy applicators, resulting expected electromagnetic field distributions, and perfusion rates in the patient.

In some embodiments, the at least one signal applicator comprises a coil.

In some embodiments, the coil comprises in the range of 5 to 100 turns.

In some embodiments, the coil comprises in the range of 10 to 60 turns.

In some embodiments, turns of the coil are uniformly spaced apart along the longitudinal axis of the coil by a pitch distance.

In some embodiments, turns of the coil are non-uniformly spaced apart along the longitudinal axis of the coil.

In some embodiments, a cross section of the coil is not circular.

In some embodiments, a spacing between turns of the coil along the longitudinal axis of the coil is adjustable.

In some embodiments, the cross section of the coil is adjustable along the longitudinal axis of the coil.

In some embodiments, the coil has a length of at least 70 centimeters.

In some embodiments, the coil has a length of at least 1 meter.

In some embodiments, the coil has an inside diameter of at least 30 cm.

In some embodiments, the length of the coil is greater than or equal to the width of the coil.

In some embodiments, the length of the coil is greater than or equal to four times the width of the coil.

In some embodiments, the coil comprises multi-layer windings.

In some embodiments, the coil is configured to open as a clamshell to admit the patient.

In some embodiments, the apparatus comprises a patient support configured to support the patient in a lying position, the patient support comprising a head support wherein the head support is outside of the coil.

In some embodiments, the RF signal has a frequency in the range of about 5 kHz to about 100 MHz.

In some embodiments, the RF signal has a frequency in the range of about 500 kHz to about 10 MHz.

In some embodiments, the controller is configured to set a frequency of the RF signal such that an electric field maximum of the electromagnetic energy signal is at a desired location relative to the at least one applicator.

In some embodiments, the controller is configured to set the frequency of the RF signal to create a standing wave in the at least one applicator.

In some embodiments, the controller is configured to set the frequency of the RF signal to create a standing wave in the at least one applicator, the standing wave having an electric field maximum in a desired location (e.g. in the patient's lung at or near a location of a volume of diseased tissue).

In some embodiments, the controller is configured to set the frequency of the RF signal to be at or near a resonant frequency of the applicator and the patient.

In some embodiments, the controller is configured to set the frequency of the RF signal to or near to an integer multiple of a resonant frequency of the applicator when the patient is present.

In some embodiments, the RF signal has a power in the range of about 500 watts to about 5 kilowatts.

In some embodiments, the controller is configured to apply time domain modulation to the RF signal.

In some embodiments, the controller is configured to control the power source to generate the RF signal as a pulsed signal and to control widths of pulses in the pulsed signal.

In some embodiments, the one or more signal applicators comprises two signal applicators connected to the power source and operative to deliver the electromagnetic energy signal into tissues of the patient.

In some embodiments, the two signal applicators comprise a first signal applicator positioned cranially from a volume to be treated and a second signal applicator positioned caudally from the volume to be treated.

In some embodiments, each of the two signal applicators is shaped to wrap or partially wrap around a circumference of the torso of the patient.

In some embodiments, the signal applicators are adjustable to conform to contours of the treated patient.

In some embodiments, the apparatus comprises cooling means for cooling the patient.

In some embodiments, the cooling means comprises a source of a cooled fluid arranged to bring the cooled fluid into thermal contact with an area of skin of the patient.

In some embodiments, the cooling means comprises a patient support comprising passages connected to carry the cooled fluid that are in thermal contact with a surface for supporting the patient.

In some embodiments, the cooling means is configured to cool the chest and back of the patient.

In some embodiments, the cooling means is configured to cool the groin of the patient.

In some embodiments, the cooling means comprises a source of chilled air.

In some embodiments, the apparatus is used in the treatment of emphysema or COPD.

One aspect of the invention provides a method for treating emphysema or COPD by selectively heating diseased lung tissue in a patient to a treatment temperature sufficient to cause a therapeutic effect in the diseased lung tissue, the method comprising: providing at least one signal applicator comprising an electrical conductor extending circumferentially around or nearly around the torso of the patient; delivering a radiofrequency (RF) signal to the at least one applicator and allowing the RF signal to be absorbed in both healthier and diseased tissues of the patient's lungs, thereby heating the tissues of the patient's lungs, whereby the heating raises the diseased tissues to temperatures exceeding a treatment threshold temperature while temperatures of the healthier tissues are kept below a safe threshold temperature lower than the treatment threshold temperature by blood circulation through the healthier tissues; keeping the temperatures of the diseased tissues above the treatment threshold temperature for a cumulative time sufficient to provide a therapeutic effect.

In some embodiments, the RF signal has an output power of at least 500 watts.

In some embodiments, the therapeutic effect is ablation of the diseased tissues.

In some embodiments, the therapeutic effect is necrosis of the diseased tissues.

In some embodiments, the therapeutic effect is induced inflammation of the diseased tissues.

In some embodiments, the RF signal creates a localized axially extending alternating electric or magnetic field within lungs of the patient.

In some embodiments, the at least one applicator comprises a coil and the patient's lungs are within the coil.

In some embodiments, the RF signal creates alternating magnetic fields extending substantially parallel to an inferior superior direction of the patient.

In some embodiments, the method comprises a strength of the alternating magnetic fields that is substantially uniform within the coil.

In some embodiments, the at least one applicator comprises a pair of electrically conductive members spaced apart along the torso of the patient.

In some embodiments, the RF signal creates localized alternating electric fields extending in an axial direction substantially parallel to an inferior superior direction of the patient.

In some embodiments the method comprises monitoring a temperature of a tissue within the patent and controlling the RF signal based on the monitored temperature. For example, controlling the RF signal may comprise one or more of setting a frequency of the RF signal, and setting an amplitude or power of the RF signal. In some embodiments the method comprising setting the frequency of the RF signal to create an electromagnetic standing wave in the patient (e.g. in the lungs of the patient).

Further aspects and example embodiments are illustrated in the accompanying drawings and/or described in the following description.

The present invention has aspects that are expressed as methods and aspects that are expressed as apparatus. Where apparatus is described herein, all the described features of the apparatus and the use of such apparatus is intended to also describe corresponding methods and where methods are described herein it is intended that the disclosure of such methods also provides apparatus configured to implement such methods.

It is emphasized that the invention relates to all combinations of the above features, even if these are recited in different claims.

BRIEF DESCRIPTION OF THE DRAWINGS

The accompanying drawings illustrate non-limiting example embodiments of the invention.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

Figure 1:
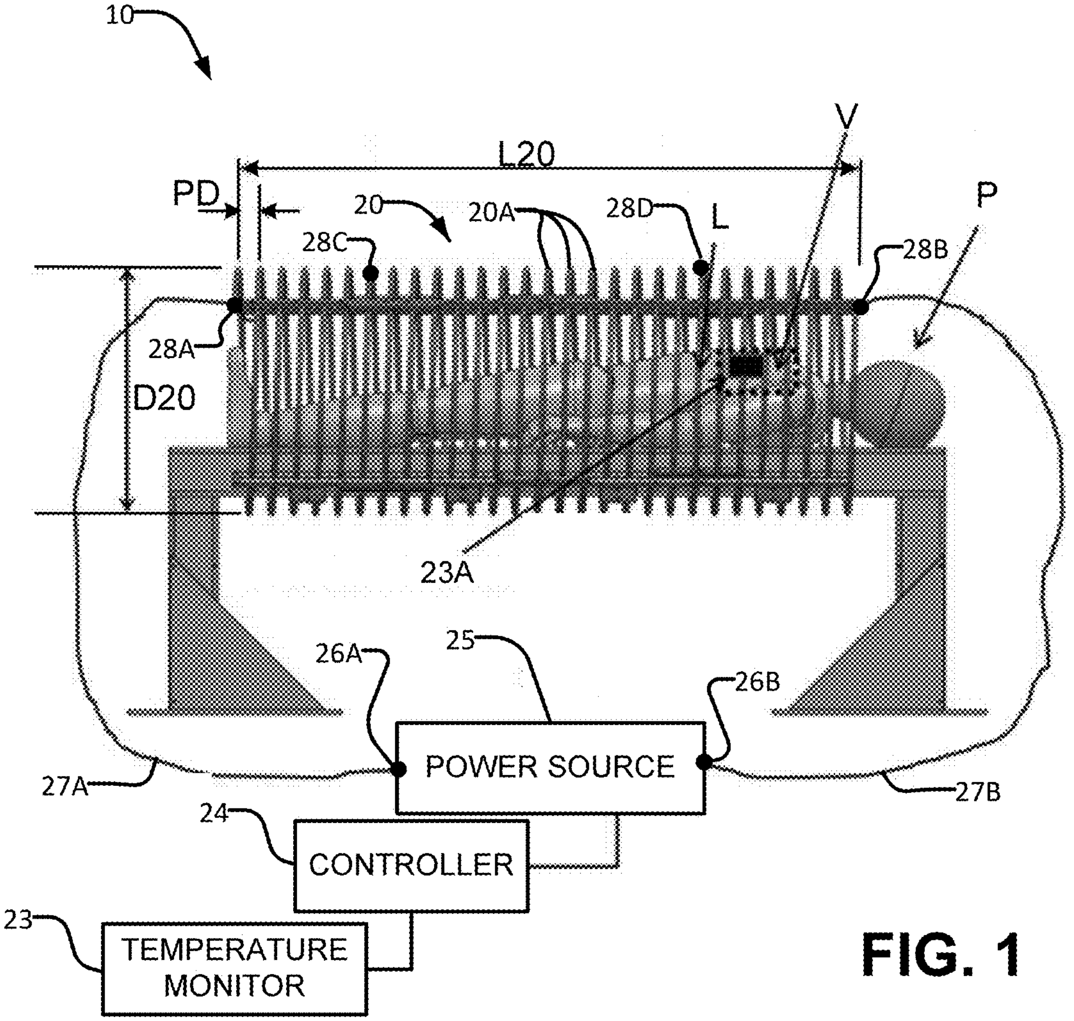
FIG. 1 illustrates apparatus according to an example embodiment.

FIG. 1 illustrates apparatus 10 according to an example embodiment. A patient P has a volume V of tissue which it is desired to treat by heating. Volume V may, for example, comprise alveoli in the patient's lung L which are impacted by emphysema.

Volume V may have relatively lower blood circulation as compared to healthier tissues in other parts of lung L such that delivery of energy at a given power density to the tissues in volume V (i.e. the energy is delivered to the tissues in volume V at a given rate which may for example be measured in watts per unit of volume in volume V which may for example be measured in $cm^3$) results in a higher temperature rise than would occur if energy at the same power density were delivered to healthier tissues in other parts of lung L. The higher temperature rise in volume V may be attributed at least in significant part to reduced blood circulation in volume V as compared to blood circulation in the healthier tissues. The circulating blood acts as a coolant which removes energy from healthier tissues at a higher rate than from volume V. This effect may be applied to heat the tissue of volume V to a temperature high enough to achieve a desired result (e.g. destruction of tissue in volume V such as tissue ablation, tissue necrosis or inducing inflammation of tissue in volume V) while the temperature in surrounding healthier tissues may remain below a safe threshold temperature such that the healthier surrounding tissues are not harmed.

For example, if one can cause each volume of the tissue of a portion of lung L that includes one or more volumes V of diseased tissue to dissipate the same amount of power per unit volume then one can choose a power level such that the one or more volumes of diseased tissue within lung L that have poor blood circulation will be heated to a temperature that is at least at a treatment temperature threshold while temperatures of volumes of healthier tissues within lung L that have better blood circulation remain below a safe temperature threshold.

Figure 1A:
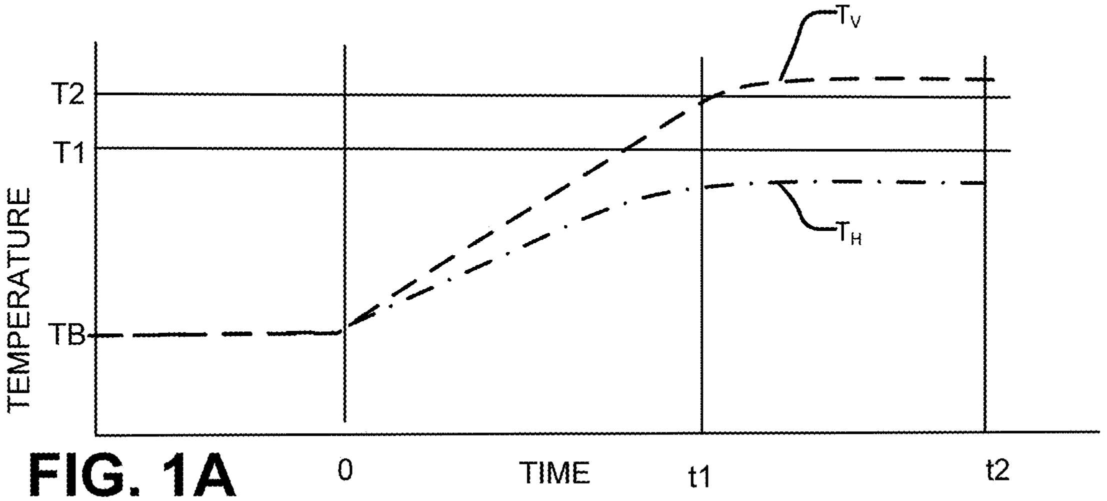
FIG. 1A is a schematic graph illustrating differential heating of diseased and healthy tissues.

FIG. 1A is a schematic graph illustrating the principle described above. Initially, the temperature $T_V$ in a volume V of diseased tissue and the temperature $T_H$ in a volume of healthy tissue are both equal to body temperature $T_B$. At time t=0 energy having a selected power density is applied to volume V and to the volume of healthy tissue. This causes temperatures $T_V$ and $T_H$ to rise. As this occurs, temperature $T_V$ tends to be higher than temperature $T_H$ because of the poor blood circulation in volume V. The power density of the applied energy and the time for which the applied energy is delivered to patient P are selected so that the temperature of healthy tissue does not exceed a safe threshold temperature T1 while the temperature in volume V reaches at least a treatment temperature threshold T2.

Apparatus 10 delivers energy to tissues in a patient by way of a signal applicator which, in apparatus 10 has the form of a coil 20 that extends around a portion of the body of patient P that includes diseased tissue to be heated.

Coil 20 is driven by a power source 25 to generate electromagnetic fields that deliver energy into the tissues of patient P. In apparatus 10, power source 25 has output terminals 26A and 26B that are connected to apply a signal to corresponding terminals of coil 20 by signal conductors 27A and 27B. In some embodiments power source 25 is connected to coil 20 at ends of coil 20 (e.g. at terminals 28A and 28B). In some embodiments, power source 25 is connected to coil 20 at terminals located away from ends of coil 20 (e.g. at terminals 28C and 28D).

A controller 24 controls power source 25 to deliver energy to the tissues of patient P to yield a desired treatment outcome. In some embodiments controller 24 is connected to receive feedback from a temperature monitor 23 that monitors temperatures at one or more points 23A in and/or near volume V.

Controller 24 may be configured to adjust the signal delivered to coil 20 to yield a desired temperature distribution in tissues of patient P. For example, it may be desired to heat volumes of diseased tissue to a temperature of at least the treatment temperature threshold T2 for a desired time period while maintaining temperatures of healthier tissues below the safe temperature threshold T1.

Controller 24 may comprise a feedback controller that has one or more inputs. The one or more inputs may include temperature measurements of tissues of patient P. Apparatus 10 includes temperature monitor 23 which acquires temperature measurements. The temperature measurements may be made with one or more temperature sensors of any suitable type(s).

Coil 20 has a number of windings 20A. In a typical, non-limiting, embodiment the number of windings is in the range of 5 to 100. In some embodiments, coil 20 has in the range of 10 to 60 windings 20A. It is not necessary that coil 20 has an integer number of windings.

Windings 20A may, for example, comprise electrically conductive wires, tubes, bars etc. Windings 20A may have cross sections: such as round, elliptical, or others. The cross sections may vary along the length of coil 20. In some embodiments windings 20A have a tubular construction.

Coil 20 is arranged to receive at least a part of the body of patient P that includes volume V. For example, where volume V is in the lungs, coil 20 may be dimensioned to receive the torso of patient P such that volume V lies inside of coil 20. For example, where patient P is an adult and coil 20 receives the torso of patient P as illustrated in FIG. 1 then coil 20 may, for example, have a diameter D20 of about 30 to 90 cm (for some larger patients, diameters toward the high end of this range or even higher may be required). Windings 20A may be wound tightly around patient P or may be dimensioned so that there is a gap between windings 20A and patient P. Where patient P is a child or other small person coil 20 may have a diameter that is smaller but large enough to extend around the torso of patient P.

Figure 1B:
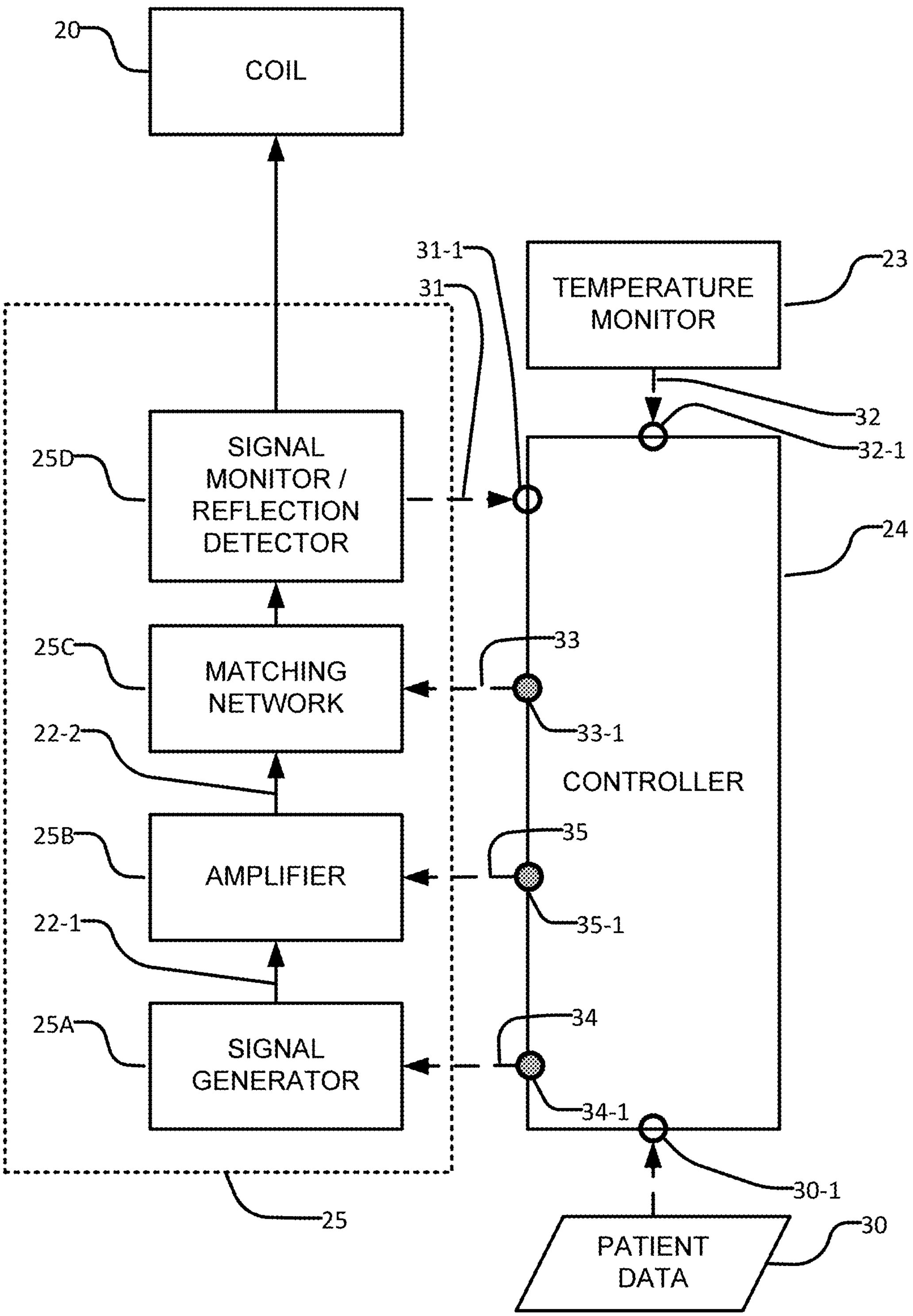
FIG. 1B is a block diagram showing an example control system for apparatus as described herein.

FIG. 1B is a block diagram that illustrates a control system that may be applied in apparatus 10 or other apparatus as described herein. In this example, power source 25 comprises a signal generator 25A that delivers an output signal 22-1 to an amplifier 25B. Signal generator 25A is operable to generate a signal which is amplified by amplifier 25B to yield an amplified signal 22-2. Amplified signal 22-2 is applied to drive coil 20.

Amplified signal 22-2 may, for example comprise a sinusoidal signal with a frequency in the range of about 5 kHz to about 100 MHz. In some embodiments, signal 22-2 has a frequency in the range of about 500 kHz to about 10 MHz. In some embodiments amplified signal 22-2 has a power in the range of about 500 watts to 5 kilowatts.

In the embodiment of FIG. 1B, power source 25 includes an impedance matching network 25C. Impedance matching network 25C is connected between the output of amplifier 25B and coil 20 and is adjustable to provide optimal power delivery to patient P. As is known to those of skill in the art of RF systems, a matching network comprises a combination of circuit elements such as capacitors, resistors and/or inductors which may be connected in various topologies to match an output impedance of amplifier 25B to an input impedance of the system comprising coil 20 and patient P. The input impedance of coil 20 and patient P depends on characteristics of coil 20 and patient P as well as characteristics of the channel that delivers the RF energy of signal 22-2 to coil 20. Matching network 25C is adjustable to maximize power delivery to patient P and minimize power reflected back to amplifier 25B.

In the embodiment illustrated in FIG. 1B, a reflection detector 25D is provided to measure RF power reflected from coil 20 and patient P. Reflection detector 25D may, for example, comprise a circulator configured to direct RF power reflected from coil 20 to an output port at which an RF power meter of any suitable kind is provided to measure the reflected power. Matching network 25C may be tuned to minimize the reflected power detected by reflection detector 25D for a particular patient P and coil 20.

Signal 22-2 causes an alternating electrical current to flow in windings 20A of coil 20. This current causes an alternating magnetic field inside coil 20. The alternating magnetic field results in an alternating electric field and induces electrical eddy currents in electrically conductive materials (e.g. the tissues of patient P) that are located within the coil 20. The combination of coil 20 and the signal provided by power source 25 may be selected such that an electric field maximum is in a plane perpendicular to the axis of coil 20 and positioned at a desired location (e.g. at the location of a treatment volume V).

In the illustrated embodiment, coil 20 has the form of a solenoid and magnetic fields within coil 20 that result from the flow of electrical current in windings 20A are directed generally parallel to a longitudinal axis of coil 20. In the illustrated embodiment, coil 20 is oriented so that the magnetic field lines extend in a superior/inferior direction (i.e. parallel to a longitudinal centerline of the patient's body). Advantageously the strength of the magnetic field is generally uniform in a cross section through coil 20 taken perpendicular to the longitudinal axis of coil 20.

FIG. 1B shows outputs and inputs of an example controller 24. Some embodiments may include all of these outputs and inputs. Other embodiments may lack some of these inputs and outputs. The same hardware optionally provides two or more or all different inputs and/or outputs of controller 24. Control signals and/or data signals may comprise analog or digital signals in any suitable format.

Controller 24 obtains patient data 30 as input 30-1. Patient data 30 may comprise one or more of:

- prescribed characteristic(s) of amplifier output signal 22-2 such as one or more of: power or power density to be delivered to a particular patient P, frequency or frequency spectrum for signal 22-2 etc.;
- a prescribed sequence for delivering power to a particular patient P;
- treatment temperature(s) and/or temperature thresholds;
- location(s) of one or more volumes V containing diseased tissue to be treated;
- physical characteristics of a particular patient P (e.g. height, weight, body fat content, girth, pulmonary circulation measures, lung volume, pretreatment imaging data (e.g. from a MRI, CT scan etc.) from which dimensions and.or tissue characteristics of the patient P may be determined); etc.

Input 30-1 may for example receive input from one or more of a graphical user interface, discrete controls, wired or wireless data interface, data store, data server, etc.

Depending on the nature of patient data 30 and the capabilities of controller 24, controller 24 may: directly receive specified characteristics for signal 22-2 or derive characteristics for signal 22-2 based on information about patient P (e.g. information of one or more of the types described above). Also depending on the nature of patient data 30 and the capabilities of controller 24, controller 24 may: receive and apply specific parameters for controlling power source 25 in patient data 30; apply built in control parameters; or derive control parameters by processing patient data 30.

Controller 24 may receive input signals 31 at an input 31-1 that indicate one or both of RF power reflected from coil 20 and RF power being delivered to coil 20. Controller 24 may output signals 33 at an output 33-1 connected to matching network 25C. Controller 24 may be configured to adjust matching network 25C by signals 33 to minimize reflected RF power from coil 20/patient P. This adjustment may be performed once prior to treatment and/or automatically on a continuing or periodic basis.

If signals 31 include a measured power level of signal 22-2, controller 24 may use the measured power level of signals 22-2 as feedback for controlling signals 22-2.

Controller 24 may receive signals 32 at input 32-1 from temperature monitor 23. Controller 24 may be configured based on signals 32 to control the power of signal 22-2, control modulation of signal 22-2 and/or stop a treatment if a measured temperature crosses a high temperature threshold.

FIG. 1B shows output 34-1 which delivers control signals 34 to control signal generator 25A. Signals 34 may, for example, control one or more of: frequency of signal 22-1, frequency spectrum of signal 22-1, pulsing of signal 22-1, and amplitude of signal 22-1.

FIG. 1B shows output 35-1 which delivers control signals 35 to control amplifier 25B. Control signals 35 may, for example, control gain of amplifier 25B.

Controller 24 may adjust the power being delivered to tissues of patient P (e.g. by signals 34 and/or 35) in response to temperature measurements (e.g. in signals 32). For example, controller 24 may control power source 25 to one or more of:

- adjust the power level of signal 22-2; e.g. to match the cooling effect of the perfusion in the healthy tissue such that it does not overheat while the diseased tissue is heated to a required temperature;
- perform time domain modulation of signal 22-2 e.g. to allow intermittent power delivery that enables the perfusion in the healthy areas to cool down the tissue below a required temperature while allowing the diseased tissue to remain at a required temperature;
- adjust a frequency of signal 22-1 e.g. to be at a resonant frequency as described below.

In some embodiments controller 24 comprises a thermal model of at least a portion of the treated patient. The thermal model correlates temperature(s) at one or more locations within the treated patient P for which temperature measurements are available to temperature(s) of one or more locations of interest for which temperature measurements may not be available. Controller 24 may be configured to apply the thermal model using the measured temperature(s) as an input of the thermal model and to regulate signal 22-2 based at least in part on an output of the thermal model.

The thermal model may, for example include one or more of: electrical and thermal properties of different tissue types in the treated patient P, distributions of the different tissue types in the treated patient P, geometry of coil 20 and resulting expected field distributions, and perfusion rates in the treated patient P.

In some embodiments controller 24 is configured to deliver power to patient P in power-on intervals spaced apart by periods in which no or reduced RF poser is delivered to patient P. For example, controller 24 may cause signal 22-2 to be applied for power-on intervals having lengths in the range of a few seconds to a few minutes separated by rests in the range of a few seconds to a few minutes. Controller 24 may be configured to control durations of the power-on intervals and/or the rests.

In some embodiments controller 24 may be configured to discontinue a treatment when a completion criterion is satisfied (such as a certain number of power-on intervals being completed, a certain temperature being achieved in diseased tissues of patient P, a certain function of temperature being achieved in diseased tissues of patient P—e.g. a time for which the temperature exceeded a threshold or the like).

In some embodiments the frequency of signal 22-1 (and 22-2) is selected to create a standing wave in coil 20. The selection of frequency typically depends on the characteristics of coil 20 (e.g. geometry, number of windings W) as well as the impedance of the patient P. In some embodiments the standing wave has a single electric field maximum. Coil 20 may be positioned relative to patient P to place the electric field maximum at or near diseased tissue to be treated in patient P.

In some embodiments the frequency of signal 22-2 is adjusted to be at or almost at the resonant frequency of coil 20 (including patient P). In some embodiments the frequency of the signal is adjusted to be at or almost at an integer multiple of the resonant frequency of coil 20 including patient P. The selection of frequency typically depends on the characteristics of the coil (e.g. geometry, number of windings 20A) and the impedance of the patient P. The frequency can be calculated in advance using these parameters (e.g. by controller 24 or in a computation external to controller 24) and later fine-tuned by measuring the electrical field in coil 20 using a field meter.

The power of signal 22-2 applied to drive coil 20 may be selected (e.g. by controlling a gain of amplifier 25B and/or adjusting an amplitude of signal 22-1) to deliver a prescribed amount of heating to the tissues of patient P. The power of the signal 22-2 applied to coil 20 may, for example, be selected based on factors such as one or more of:

- the weight of patient P;
- an estimate of a weight of a part of patient P (e.g. lungs of patient P);
- the height and/or girth of patient P;
- RF absorption of the tissues of patient P within coil 20 (which depends mostly on the percentage of fat in the body of patient P);
- the RF coupling between coil 20 and tissues of patient P (which depends on the frequency of the signals as well as the dimensions and geometry of coil 20); and
- a measure of the pulmonary circulation of patient P.

In some embodiments temperature monitor 23 is of a type operable to perform non-invasive temperature sensing. For example, tissue temperatures may be measured by processing ultrasound signals or magnetic resonance imaging (MRI) signals.

In some embodiments the temperature measurements are performed using non-contact temperature sensing systems (e.g. processing MRI data). In some such embodiments, coil 20 is located inside the MRI system. Controller 24 may be configured to interrupt delivering signal 22-2 to coil 20 to permit temperature measurements to be made.

In some embodiments the temperature measurements are performed using an invasive temperature sensor that is placed in patient P (e.g. through a needle or catheter).

In some embodiments apparatus as described herein is combined with an imaging system (for example an ultrasound imaging system or MRI system). The imaging system may be used for temperature monitoring and/or for imaging patient P.

Where apparatus 10 is applied to treat diseased tissues in lungs of patient P, coil 20 preferably has a length sufficient that at least the lungs L of patient P are received within coil 20. It is generally desirable that the head of patient P is shielded from radiofrequency radiation and/or outside of coil 20.

FIG. 1 depicts a non-limiting example embodiment in which the length L20 of coil 20 is close to the height of patient P. In FIG. 1, the windings of coil 20 extend around the body of patient P and Volume V includes the lungs L.

Other configurations are also possible. For example coil 20 may have a shorter length so that coil 20 receives the torso of patient P inside coil 20. Length L20 may be selected based on the properties of patient P.

Coil 20 may be circular in cross section but this is not mandatory. In some embodiments coil 20 is flattened. For example, coil 20 may have an oval or elliptical cross sectional shape.

Figure 1C:
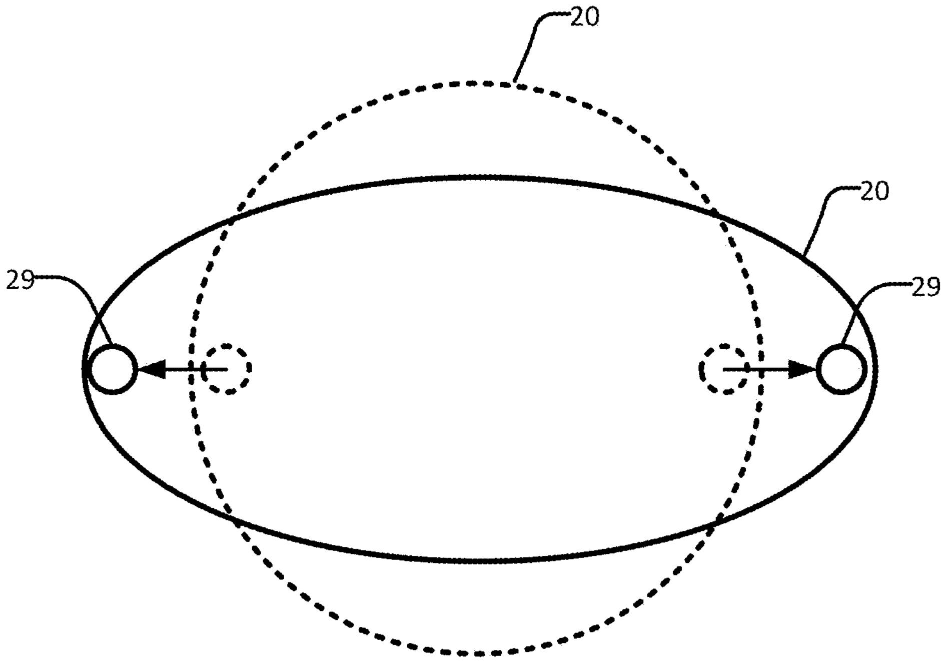
FIG. 1C is a schematic cross section of a coil illustrating one way to adjust a cross sectional shape of the coil.

In some embodiments a cross sectional shape of coil 20 is adjustable. For example, the material of coil 20 may be elastically deformable so that coil 20 may be deformed into a configuration such that the bore of coil 20 is expanded and the height of coil 20 is reduced. This may be done, for example by spreading coil 20. FIG. 1C schematically shows, spreading coil 20 by separating electrically non-conductive bars 29.

In some embodiments a cross sectional shape of coil 20 is independently adjustable along the longitudinal axis of coil 20. Such adjustment can be made depending on the properties of the patient. Adjustment of the cross-sectional shape of coil 20 may be achieved by making the turns of coil 20 of a flexible conductive material (e.g. flexible wires, flexible bars) and deforming the coil by displacing the turns of coil 20 to take on a desired shape.

In some embodiments the geometry of coil 20 is varied along the length of coil 20. For example, the turns of coil 20 may be made tighter (smaller pitch distance PD between adjacent turns). For example, it may be beneficial to wind coil 20 more tightly (smaller PD) around certain areas for best results. In some embodiments, end portions of coil 20 are wound more tightly than an intermediate portion of coil 20 between the end portions.

Windings 20A are spaced apart along length L20. Windings 20A may be uniformly or non-uniformly spaced apart from one another (i.e pitch distance PD may be uniform or non-uniform).

In some embodiments the spacing between windings 20A along the longitudinal axis of coil 20 is adjustable. In such embodiments the spacing between windings 20A may be adjusted depending on the properties of the patient. This could be accomplished, for example, by using flexible elements, such as a coaxial network cable or other flexible wire as windings of coil 20 and supporting the windings on an adjustable frame made of material that does not absorb radiofrequency (RF) radiation.

In some embodiments the diameter of coil 20 varies along the length of coil 20.

Figure 2:
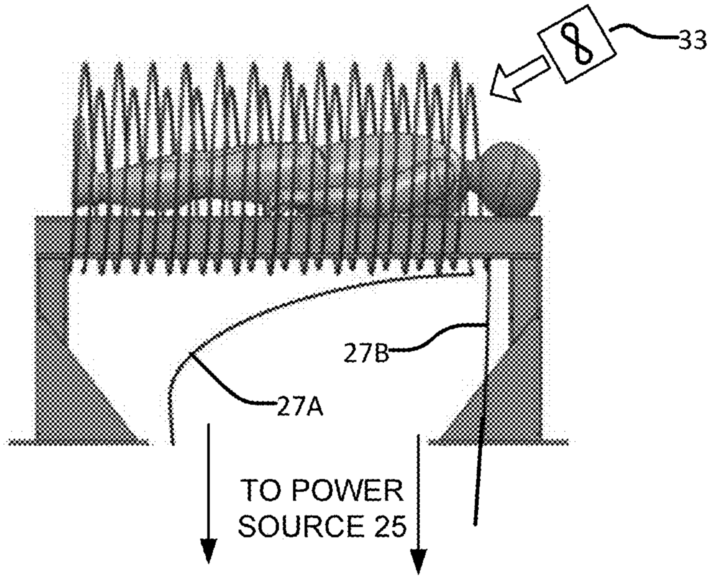
FIG. 2 is a side elevation of apparatus according to an example embodiment which includes a multi-layer coil.

In some embodiments coil 20 has multi-layer windings as shown, for example in FIG. 2

Figure 3:
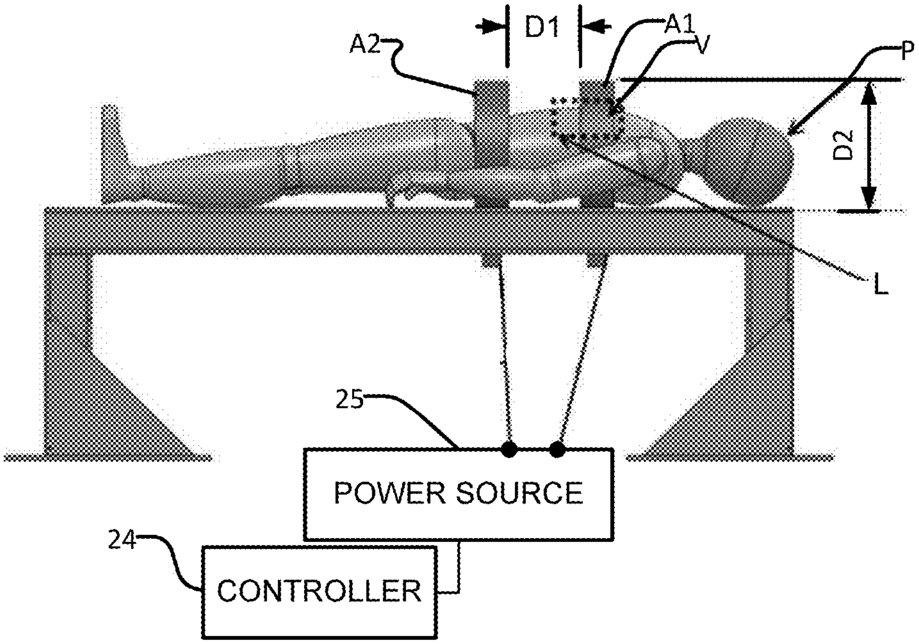
FIG. 3 is a side elevation of another example apparatus which includes a pair of spaced apart applicators that extend circumferentially or partially circumferentially around a patient.

The technology described herein may be varied. For example, instead of a single coil 20, apparatus as described herein may include two or more applicators that cooperate to deliver energy into the tissues of patient P. For example, FIG. 3 shows example apparatus 40 which is like apparatus 10 except that it includes two spaced apart applicators A1 and A2. Each of Applicators A1 and A2 is configured to wrap or partially wrap around the circumference of the torso of patient P. Applicators A1 and A2 may be ring shaped. Applicators A1 and A2 may, for example, have circular, elliptical or obround cross sections.

In some embodiments applicators A1 and A2 extend completely (360 degrees) around the torso of patient P. In some embodiments, one or both of applicators A1 and/or A2 extend through an angle of at least 180 degrees or at least 230 degrees or at least 250 degrees or at least 270 degrees or at least 300 degrees or at least 330 degrees relative to a point that is centered side to side and up and down inside the applicator in a plane of the applicator. In some embodiments applicators A1 and A2 extend circumferentially nearly around a patient P. In this disclosure. "nearly around" when applied to an applicator means that the applicator extends through an angle in the range of 180 degrees to 360 degrees relative to a point that is centered side to side and up and down inside the applicator in a plane of the applicator.

For example, applicators A1 and A2 may be made of thin electrically conductive sheets (e.g. copper foil) formed to extend around the body of patient P.

When an output signal 22-2 of a power source 25 is delivered to applicators A1 and A2, varying electric fields between applicators A1 and A2 cause energy to be delivered to and dissipated in tissues of patient P.

In apparatus 40, one or both of applicators A1 and A2 overlaps with a volume V within which there is tissue to be treated. In another example embodiment, applicators A1 and A2 are positioned symmetrically relative to a volume V that includes tissues to be treated. For example, applicator A1 may be positioned cranially relative to a treatment volume V and applicator A2 may be positioned caudally relative to treatment volume V.

In another example embodiment, applicators A1 and/or A2 are configured to form unclosed sections of a ring. The applicators may be connected to terminals of a power source 25. For example, one of the applicators may be grounded and the other applicator may be connected to a terminal of a power source 25 that carries a signal 22-1 (e.g. a varying voltage signal).

The technology described herein may be further varied. For example, Apparatus 10 and Apparatus 40 may be positioned vertically rather than horizontally such that patient P stands or sits inside coil 20 or inside applicators A1 and A2. This saves the need for a table for patient P to lie on and may have further advantages.

Further variations of the disclosed technology are also possible. For example, a coil 20 and/or applicators A1, A2 may be configured to open like a clamshell to receive a patient P. Windings of a coil 20 or applicators A1, A2 may be split along an opening line of the clamshell and may make electrical contact when the clamshell is closed.

In some embodiments a coil 20 is wound around patient P as patient P lies on a table, sits or stands.

In some embodiments shielding is provided to shield certain parts of the patient from RF radiation. Shielding may for example be provided by shields made of meshes, grids or continuous sheets of electrically conductive material. The shields are optionally transparent to allow viewing the shielded parts.

In some embodiments the entire apparatus including patient P is contained within a shielding structure such as a Faraday cage or any other enclosure made of conductive material. Such a structure may prevent radiofrequency radiation from the apparatus from interfering with other systems. A shielding structure may be continuous or made of a wire mesh. In some embodiments suitable RF shielding is embedded into or supported on walls of a room in which the apparatus is located.

Some embodiments comprise means for locally cooling the skin of patient P (e.g. by a flow of air, water or another liquid either directly in contact with the skin or through a bladder placed in contact with the area(s) to be cooled). Such cooling may help to protect the skin and surface tissues of patient P from being overheated, improve comfort for patient P and/or help to remove heat from the blood of patient P.

In some embodiments cooling is provided to areas of patient P where there is significant blood circulation close to the skin (e.g. in the area of the groin). FIG. 2 shows a fan 33 arranged to deliver a stream of cooled air to patient P. In some embodiments patient P is supported on a cooled support (e.g. a table or mat that includes passages which carry a cooled gas or liquid or a mesh through which a cooled gas may be delivered to remove heat from the skin of patient P).

Signals as described herein may be delivered from their sources to their destinations in any suitable manner. For example, control signals may be carried by electrical conductors, optical conductors, wireless communication technology or the like. Power signals such as output signal 22-2 of a power source 25 may be delivered to a destination by suitable electrical conductors such as coaxial cables, wires, waveguides, inductive or capacitive couplings, free space transmission etc.

A controller 24 may be implemented by way of any suitable technology including specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), field programmable gate arrays ("FPGAs") and configurable neural networks such as convolutional neural networks ("CNNs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a controller 24 may implement methods as described herein by executing software instructions in a program memory accessible to the processors.

INTERPRETATION OF TERMS

Unless the context clearly requires otherwise, throughout the description and the claims:

- "comprise", "comprising", and the like are to be construed in an inclusive sense, as opposed to an exclusive or exhaustive sense; that is to say, in the sense of "including, but not limited to";
- "connected", "coupled", or any variant thereof, means any connection or coupling, either direct or indirect, between two or more elements; the coupling or connection between the elements can be physical, logical, or a combination thereof;
- "herein", "above", "below", and words of similar import, when used to describe this specification, shall refer to this specification as a whole, and not to any particular portions of this specification;
- "or", in reference to a list of two or more items, covers all of the following interpretations of the word: any of the items in the list, all of the items in the list, and any combination of the items in the list;
- the singular forms "a", "an", and "the" also include the meaning of any appropriate plural forms.

Words that indicate directions such as "vertical", "transverse", "horizontal", "upward", "downward", "forward", "backward", "inward", "outward", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Some aspects of the invention may also be provided in the form of a program product. The program product may comprise any non-transitory medium which carries a set of computer-readable instructions which, when executed by a data processor, cause the data processor to execute a method of the invention. For example, a program product may store computer executable instructions that, when executed by one or more processors cause the execution of one or more control methods performed by controller 24. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

Where a component (e.g. a coil, applicator, amplifier, matching network, power source, controller, table, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

For example, while various methods are presented as proceeding in a given sequence, alternative examples may proceed in a different sequence or perform routines having steps, or employ systems having blocks, in a different order. Steps, acts, processes or blocks may be deleted, moved, added, subdivided, combined, and/or modified to provide alternative or subcombinations. Described processes or blocks may be implemented in a variety of different ways. Also, when processes or blocks are at times shown as being performed in series, certain processes or blocks may instead be performed in parallel, or may be performed at different times.

Various features are described herein as being present in "some embodiments". Such features are not mandatory and may not be present in all embodiments. Embodiments of the invention may include zero, any one or any combination of two or more of such features. All possible combinations of such features are contemplated by this disclosure even where such features are shown in different drawings and/or described in different sections or paragraphs. This is limited only to the extent that certain ones of such features are incompatible with other ones of such features in the sense that it would be impossible for a person of ordinary skill in the art to construct a practical embodiment that combines such incompatible features. Consequently, the description that "some embodiments" possess feature A and "some embodiments" possess feature B should be interpreted as an express indication that the inventors also contemplate embodiments which combine features A and B (unless the description states otherwise or features A and B are fundamentally incompatible).

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. Apparatus for treating emphysema or chronic obstructive pulmonary disease, COPD, by selectively heating diseased lung tissue in a patient to a temperature above a treatment threshold temperature for a cumulative time sufficient to cause a therapeutic effect in the diseased lung tissue, the apparatus comprising:

at least one signal applicator comprising an electrical conductor dimensioned to extend circumferentially around or nearly around the torso of the patient;

a power source connected to deliver a radiofrequency (RF) signal to the at least one applicator, the power source comprising an impedance matching network operative to match an output impedance of the power source to an input impedance of the signal applicator;

a controller operatively associated with the power source and configured to control the power source to apply the RF signal to the applicator;

wherein the controller is configured to set the frequency of the RF signal to be at or near an integer multiple of a resonant frequency of the applicator when the patient is present to create localized alternating electric fields extending in an axial direction substantially parallel to an inferior-superior direction of the patient;

the applicator, when energized by the RF signal, operative to couple an electromagnetic energy signal into tissues of the patient, such that the tissues of the patient are heated by the electromagnetic energy signal and the diseased tissue is selectively heated to higher temperatures than healthy tissues due to relatively lower blood circulation to the diseased tissue when compared to blood circulation to the healthy tissues.

2. The apparatus according to claim 1 comprising a temperature monitor operative to monitor a temperature at one or more locations within the tissue of the patient wherein the controller is connected to receive a temperature signal from the temperature monitor indicating the temperature at the one or more locations, and the controller is configured to apply feedback control to the power source to regulate the electromagnetic energy signal delivered into the patient based at least in part on the temperature signal.

3. The apparatus according to claim 2 wherein the temperature monitor is a non-invasive temperature monitor.

4. The apparatus according to claim 2 wherein the temperature monitor comprises a magnetic resonance imaging (MRI) imaging system and a processor configured to process a MRI signal provided by the MRI imaging system to determine the temperature corresponding to each of the one or more locations.

5. The apparatus according to claim 2 wherein the temperature monitor comprises an ultrasound imaging system and a processor configured to process an ultrasound signal provided by the US ultrasound imaging system to determine the temperature corresponding to each of the one or more locations.

6. The apparatus according to claim 2 wherein the controller is configured to control one or more parameters of the RF signal until the temperature at the location is at least equal to the treatment threshold temperature for the cumulative time.

7. The apparatus according to claim 2 wherein:

the controller comprises a model of at least a portion of the patient, the model correlating temperatures at the one or more locations to a temperature of a location of interest; and the controller is configured to apply the model using the temperature signal as an input and to regulate the heating energy based at least in part on an output of the model.

8. The apparatus according to claim 7 wherein the model comprises one or more of: electrical and thermal properties of different tissue types in the patient, distributions of the different tissue types in the patient, geometry of one or more electromagnetic energy applicators, resulting expected electromagnetic field distributions, and perfusion rates in the patient.

9. The apparatus according to claim 1 wherein the at least one signal applicator comprises a coil.

10. The apparatus according to claim 9 wherein the coil comprises in the range of 5 to 100 turns.

11. The apparatus according to claim 9 wherein a cross section of the coil is not circular.

12. The apparatus according to claim 9 wherein a spacing between turns of the coil along the longitudinal axis of the coil is adjustable.

13. The apparatus according to claim 9 wherein the cross section of the coil is adjustable along the longitudinal axis of the coil.

14. The apparatus according to claim 9 wherein the length of the coil is greater than or equal to the width of the coil.

15. The apparatus according to claim 9 wherein the coil comprises multi-layer windings.

16. The apparatus according to claim 9 wherein the coil is configured to open as a clamshell to admit the patient.

17. The apparatus according to claim 1 wherein the RF signal has a frequency in the range of about 5 kHz to about 100 MHZ.

18. The apparatus according to claim 1 wherein the controller is configured to set a frequency of the RF signal such that an electric field maximum of the electromagnetic energy signal is at a desired location relative to the at least one applicator.

19. The apparatus according to claim 1 wherein the controller is configured to set the frequency of the RF signal to create a standing wave in the at least one applicator.

20. The apparatus according to claim 1 wherein the controller is configured to set the frequency of the RF signal to create a standing wave in the at least one applicator, the standing wave having an electric field maximum in a desired location.

21. The apparatus according to claim 1 wherein the controller is configured to at least one of: apply time domain modulation to the RF signal; and control the power source to generate the RF signal as a pulsed signal and to control widths of pulses in the pulsed signal.

22. The apparatus according to claim 1 wherein the at least one signal applicator comprises two signal applicators connected to the power source and operative to deliver the electromagnetic energy signal into tissues of the patient, the two signal applicators comprising a first signal applicator positioned cranially from a volume to be treated and a second signal applicator positioned caudally from the volume to be treated.

23. The apparatus according to claim 22 wherein each of the two signal applicators is shaped to wrap or partially wrap around a circumference of the torso of the patient.

24. The apparatus according to claim 22 wherein the signal applicators are adjustable to conform to contours of the treated patient.

25. The apparatus according to claim 1 comprising cooling means for cooling the patient.

26. The apparatus according to claim 25 wherein the cooling means comprises at least one of: a source of a cooled fluid arranged to bring the cooled fluid into thermal contact with an area of skin of the patient; a patient support comprising passages connected to carry the cooled fluid that are in thermal contact with a surface in contact with the patient; and a source of chilled air.

27. The apparatus according to claim 25 wherein the cooling means is configured to cool at least one of a chest and back of the patient and a groin of the patient.

28. A method for treating emphysema or chronic obstructive pulmonary disease, COPD, by selectively heating diseased lung tissue in a patient to a treatment temperature sufficient to cause a therapeutic effect in the diseased lung tissue, the method comprising:

providing at least one signal applicator comprising an electrical conductor extending circumferentially around or nearly around the torso of the patient;

delivering a radiofrequency (RF) signal to the at least one applicator and allowing the RF signal to be absorbed in both healthier and diseased tissues of the patient's lungs, thereby heating the tissues of the patient's lungs, whereby the heating raises the diseased tissues to temperatures exceeding a treatment threshold temperature while temperatures of the healthier tissues are kept below a safe threshold temperature lower than the treatment threshold temperature by blood circulation through the healthier tissues;

keeping the temperatures of the diseased tissues above the treatment threshold temperature for a cumulative time sufficient to provide a therapeutic effect;

wherein delivering the RF signal to the at least one applicator comprises setting the frequency of the RF signal to be at or near an integer multiple of a resonant frequency of the applicator when the patient is present to create localized alternating electric fields extending in an axial direction substantially parallel to an inferior-superior direction of the patient.

* * * * *